US010118776B2

(12) United States Patent
Hughes

(10) Patent No.: US 10,118,776 B2
(45) Date of Patent: Nov. 6, 2018

(54) DEVICE AND METHOD FOR DELIVERING A LABORATORY SAMPLE CARRIER FROM A STACK OF SAMPLE CARRIERS

(71) Applicant: Thomas Fergus Hughes, Netherfield (GB)

(72) Inventor: Thomas Fergus Hughes, Netherfield (GB)

( * ) Notice: Subject to any disclaimer, the term of this patent is extended or adjusted under 35 U.S.C. 154(b) by 0 days.

(21) Appl. No.: 15/502,427

(22) PCT Filed: Aug. 19, 2015

(86) PCT No.: PCT/GB2015/052404
§ 371 (c)(1),
(2) Date: Feb. 7, 2017

(87) PCT Pub. No.: WO2016/030663
PCT Pub. Date: Mar. 3, 2016

(65) Prior Publication Data
US 2017/0233200 A1 Aug. 17, 2017

(30) Foreign Application Priority Data
Aug. 28, 2014 (GB) .................................. 1415242.5

(51) Int. Cl.
*G07F 11/16* (2006.01)
*B65G 59/06* (2006.01)
(Continued)

(52) U.S. Cl.
CPC ............. *B65G 59/062* (2013.01); *B65H 3/24* (2013.01); *G01N 35/00* (2013.01); *G07F 11/16* (2013.01);
(Continued)

(58) Field of Classification Search
CPC .................................................. B65G 59/067
(Continued)

(56) References Cited

U.S. PATENT DOCUMENTS 324,717 A * 8/1885 Meyers ................... G07F 11/16
206/380
1,813,713 A * 7/1931 Selby ...................... G07F 11/18
194/260
(Continued)

FOREIGN PATENT DOCUMENTS

GB 2 235 163 A 2/1991

OTHER PUBLICATIONS

PCT/GB2015/052404, International Search Report and Written Opinion, dated Oct. 29, 2015.
(Continued)

*Primary Examiner* — Gregory W Adams
(74) *Attorney, Agent, or Firm* — Fay Sharpe LLP

(57) ABSTRACT

A device and method for delivering a laboratory sample carrier from a stack of sample carriers includes providing a retaining mechanism that retains the stack of laboratory sample carriers, and an ejector mechanism including a displaceable mechanism comprising a carrier support portion and a carrier transporting portion which are hingeably interconnected. The stack is supported by the carrier transporting portion and the carrier transporting portion is supported by a carrier transporting portion support of the ejector mechanism when the displaceable mechanism is in a first carrier receiving position and configuration. The displaceable mechanism is displaced from the first carrier receiving position and configuration to a second carrier release position and configuration by a further displacement mechanism of the ejector mechanism. This involves moving a lower-most carrier from the bottom of the stack in a carrier accommodating region of the carrier transporting portion as the displaceable mechanism is displaced from the first carrier receiving position and configuration. The displaceable mechanism is displaced such that the carrier transporting portion moves past the carrier transporting portion
(Continued)

support and drops so that the displaceable mechanism adopts the second carrier release position and configuration and the carrier in the carrier accommodating region is released. The stack is supported with the carrier support portion when the displaceable mechanism is in the second carrier release position and configuration.

10 Claims, 2 Drawing Sheets

(51) Int. Cl.
*B65H 3/24* (2006.01)
*G01N 35/00* (2006.01)

(52) U.S. Cl.
CPC .............. *G01N 2035/00089* (2013.01); *G01N 2035/00861* (2013.01)

(58) Field of Classification Search
USPC ......... 221/187, 256, 268, 270, 272, 295, 90, 221/10.14, 271; 271/10.14, 271; 414/796.1, 796.3, 797.4, 797.5, 797.6, 414/797.7, 797.9, 798.5, 798.7
See application file for complete search history.

(56) References Cited

U.S. PATENT DOCUMENTS

| | | | | |
|---|---|---|---|---|
| 1,973,867 A * | 9/1934 | Cook | ......................... | A47F 1/10 221/155 |
| 2,601,118 A * | 6/1952 | Guesmer | ................... | A47F 1/10 221/206 |
| 2,738,102 A * | 3/1956 | Shepherd | ................ | G07F 11/16 221/18 |
| 3,161,320 A * | 12/1964 | Swanson | ................ | A47G 19/32 221/255 |
| 3,340,790 A * | 9/1967 | Simjian | ..................... | A47F 1/00 221/150 HC |
| 3,957,175 A * | 5/1976 | Gordon | ................. | G07F 11/045 221/215 |
| 4,305,538 A * | 12/1981 | Schultz | ................ | B27M 3/0073 144/1.1 |
| 4,344,611 A * | 8/1982 | Morita | ..................... | B65H 3/24 271/129 |
| 4,405,124 A * | 9/1983 | Watanabe | ................. | B65H 3/24 271/135 |
| 4,619,375 A * | 10/1986 | Kathari | ..................... | B65H 3/24 221/186 |
| 4,653,667 A * | 3/1987 | Wettlen | .................... | G07F 17/42 221/236 |
| 4,865,222 A * | 9/1989 | Sullivan | ............... | B65G 59/067 221/241 |
| 5,163,581 A * | 11/1992 | Lombardi, Jr. | .... | A45D 40/0087 132/320 |
| 5,232,123 A * | 8/1993 | Richardson | ............. | G07F 11/22 221/155 |
| 5,323,920 A * | 6/1994 | Harris | ........................ | A47F 1/10 211/59.2 |
| 5,511,690 A | 4/1996 | Calhoun et al. | | |
| 5,963,368 A * | 10/1999 | Domanik | ............. | G02B 21/365 356/72 |
| 6,098,839 A | 8/2000 | Hunnell | | |
| 6,789,996 B2 * | 9/2004 | Yuyama | ................... | G07F 11/04 221/251 |
| 7,553,451 B2 * | 6/2009 | Fichera | ............. | G01N 35/00029 422/560 |
| 7,694,847 B2 * | 4/2010 | Iwamoto | ................ | B23P 19/003 221/213 |
| 8,013,884 B2 * | 9/2011 | Schlinkmann | ........... | B41J 3/407 347/171 |
| 8,425,176 B2 * | 4/2013 | Forcina | ................. | G03B 42/045 221/113 |
| 8,609,042 B2 * | 12/2013 | Walter | ...................... | B01L 9/52 347/102 |
| 2006/0073073 A1 | 4/2006 | Fichera | | |
| 2008/0094804 A1 | 4/2008 | Reynolds et al. | | |

OTHER PUBLICATIONS

GB 1415242.5 Search Report Under Section 17(5), dated Jan. 29, 2015.

* cited by examiner

DEVICE AND METHOD FOR DELIVERING A LABORATORY SAMPLE CARRIER FROM A STACK OF SAMPLE CARRIERS

This application is a Submission Under 35 U.S.C. 371 of International Application No. PCT/GB2015/052404, International Filing Date 19 Aug. 2015, which claims the priority benefit of GB 1415242.5, filed 28 Aug. 2014, the disclosures of which are incorporated herein by reference.

The present invention relates to a device and method for delivering a laboratory sample carrier from a stack of sample carriers where the sample carriers may be laboratory slides.

A conventional printer for printing on laboratory slides has a printing mechanism that prints on slides that are orientated in a horizontal plane. The printer may have a delivery device for delivering an unprinted slide from a stack of unprinted slides to the printing mechanism. The delivery device may remove a slide from the stack and keep that slide in the same orientation as it is delivered to the printing mechanism.

However, for a printer arranged to print on a laboratory slide that is arranged to travel through the printer vertically or inclined such that the slide travels under the influence of gravity, the delivery device described above would be unable to deliver a slide in the correct orientation to a printing mechanism of the printer from a stack of slides.

Also, for a particular case there may be laboratory slides of different types that need to be printed on. Slides of one type may be stacked in, say, a hopper for delivery to a slide printer. If a different type of slide needs to be printed then the slides of one type would need to be unloaded from the hopper and replaced with the slides of the different type. Alternatively, the hopper and its one type of slide would need to be replaced by a different hopper holding a different type of slide.

It is an object of the present invention to provide a device and method to alleviate at least one of the above-mentioned problems.

According to one aspect of the present invention there is provided a device for delivering a laboratory sample carrier from a stack of sample carriers, the device comprising: means for retaining a stack of laboratory sample carriers; and an ejector mechanism comprising: a displaceable mechanism comprising a carrier support portion and a carrier transporting portion which are hingeably interconnected, the carrier transporting portion having a carrier accommodating region; displacement means for displacing the displaceable mechanism from a first carrier receiving position and configuration to a second carrier release position and configuration, the carrier transporting portion arranged to support the stack when the displaceable mechanism is in the first carrier receiving position and configuration, the displaceable mechanism arranged to move a lowermost carrier from the bottom of the stack in the carrier accommodating region as the displaceable mechanism is displaced from the first carrier receiving position and configuration, and the carrier support portion is arranged to support the stack when the displaceable mechanism is in the second carrier release position and configuration; and a carrier transporting portion support for supporting the carrier transporting portion when the displaceable mechanism is in the first carrier receiving position and configuration but does not support the carrier transporting portion when the displaceable mechanism is in the second carrier release position and configuration thereby allowing the carrier transporting portion to drop to a carrier release position to release any said carrier from the carrier accommodating region.

The device may thus re-orientate a laboratory sample carrier, which may be a slide from a stack of such carriers, for delivery to a printer for marking a laboratory sample carrier wherein the carrier is arranged to travel through the printer vertically or inclined such that the carrier travels under the influence of gravity. The displacement means can be a simple linear reciprocating displacement means and therefore include few moving parts and avoid any requirement for a more complicated mechanism.

The carrier support portion may have an abutment for moving said lowermost carrier from the bottom of the stack.

The carrier transporting portion may be arranged to rotate relative to the carrier support portion when the displacement means displaces the displaceable mechanism from the first carrier receiving position and configuration to the second carrier release position and configuration. The carrier transporting portion support may include biasing means for biasing the displaceable mechanism towards the means for retaining the stack of carriers. The biasing means reduces friction between the displaceable mechanism and the carrier transporting portion support when the displaceable mechanism is displaced from the first carrier receiving position and configuration to the second carrier release position and configuration.

The device may include release means for releasing a said carrier from the carrier accommodating region when the displaceable mechanism reaches the second carrier release position and configuration. The carrier transporting portion may have a stop for preventing a said carrier held in the carrier accommodating region from dropping from the carrier transporting portion before the displaceable mechanism reaches the second carrier release position and configuration. The release means may comprise a release surface positioned to engage a carrier in the carrier transporting portion and displace the carrier past the stop of the carrier transporting portion when the displaceable mechanism reaches the second carrier release position and configuration. The release surface provides a simple way of releasing a carrier in the carrier transporting portion when the displaceable mechanism reaches the second carrier release position and configuration. The carrier transporting portion support may be part of a base of the ejector mechanism and the release means comprise part of the base. When the displaceable mechanism reaches the second carrier release position and configuration, the carrier transporting portion may engage the base and the release means of the base causes the carrier in the carrier transporting portion to be released.

The stack retaining means may comprise a stack retaining stop for preventing carriers other than the lowermost carrier of the stack from being moved when said lowermost carrier is moved from the bottom of the stack.

There may be provided a combination of the device as described above, and an apparatus for marking a laboratory sample carrier that is arranged to travel through the apparatus vertically or inclined such that the carrier travels under the influence of gravity, the device being positioned to drop the released carrier into the apparatus for marking. The apparatus for marking may be arranged to receive by hand a carrier to be marked as well as to receive a carrier from the device. Thus, a routine type of laboratory sample carrier could be stacked in the device and special types of laboratory sample carriers could be loaded by hand into the apparatus for marking. This would provide a significant time saving since for a user to mark the special types of carriers he would not need to remove the routine carriers from the stack or remove the means for retaining the stack of carriers or even remove the whole device from the apparatus for marking.

According to another aspect of the present invention there is provided a method for delivering a laboratory sample carrier from a stack of sample carriers, the method comprising the steps of: providing a displaceable mechanism comprising a carrier support portion and a carrier transporting portion which are hingeably interconnected; retaining the stack of laboratory sample carriers; supporting the stack with the carrier transporting portion and supporting the carrier transporting portion with a carrier transporting portion support when the displaceable mechanism is in a first carrier receiving position and configuration; and displacing the displaceable mechanism from the first carrier receiving position and configuration to a second carrier release position and configuration, the displacing step comprising: (i) moving a lowermost carrier from the bottom of the stack in a carrier accommodating region of the carrier transporting portion as the displaceable mechanism is displaced from the first carrier receiving position and configuration; (ii) displacing the displaceable mechanism such that the carrier transporting portion moves past the carrier transporting portion support and drops so that the displaceable mechanism adopts the second carrier release position and configuration and the carrier in the carrier accommodating region is released; and (iii) supporting the stack with the carrier support portion when the displaceable mechanism is in the second carrier release position and configuration.

An embodiment of the present invention will now be described, by way of example, with reference to the accompanying schematic drawings, in which.

Figure 1:
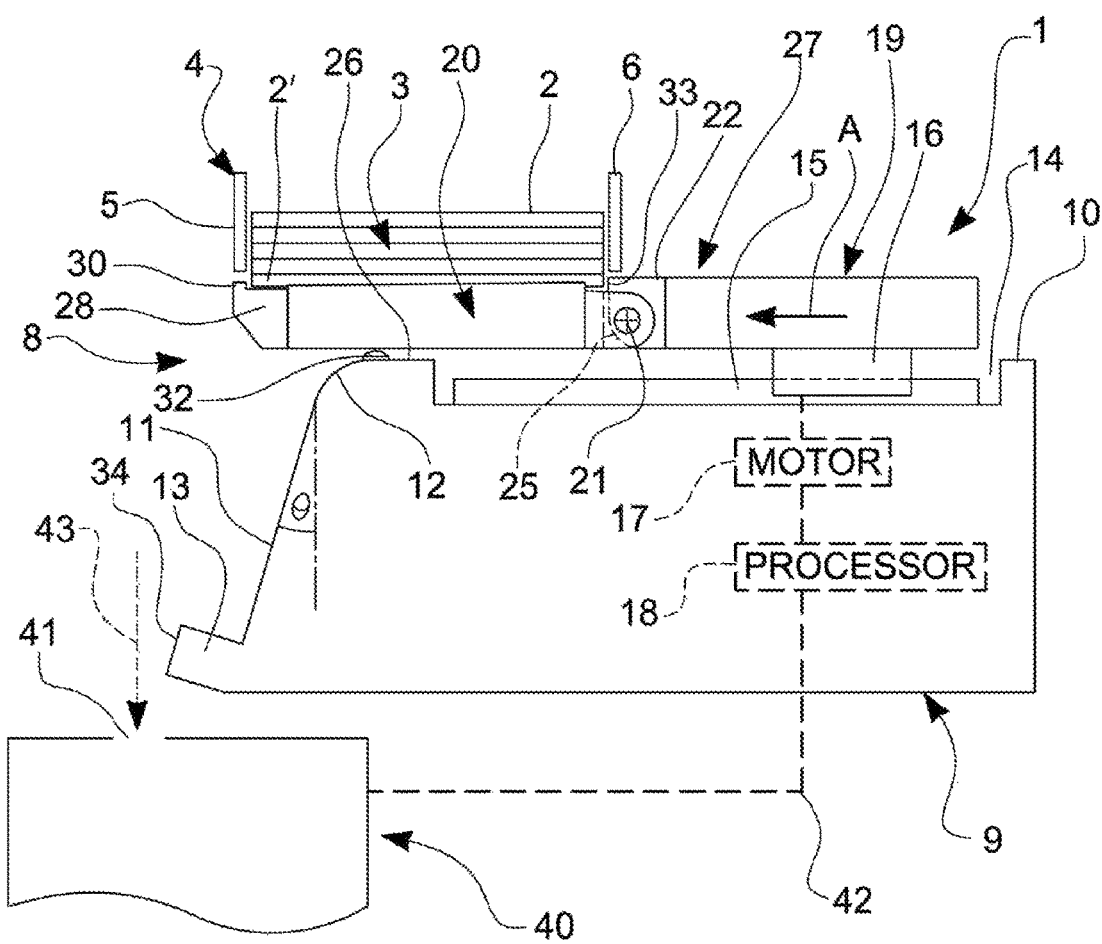
FIG. 1 is a side view of a device for delivering a laboratory sample carrier from a stack of sample carriers according to one embodiment of the invention, and a printer for marking laboratory sample carriers, a displaceable mechanism of the device being shown in a first carrier receiving position and configuration.
Figure 2:
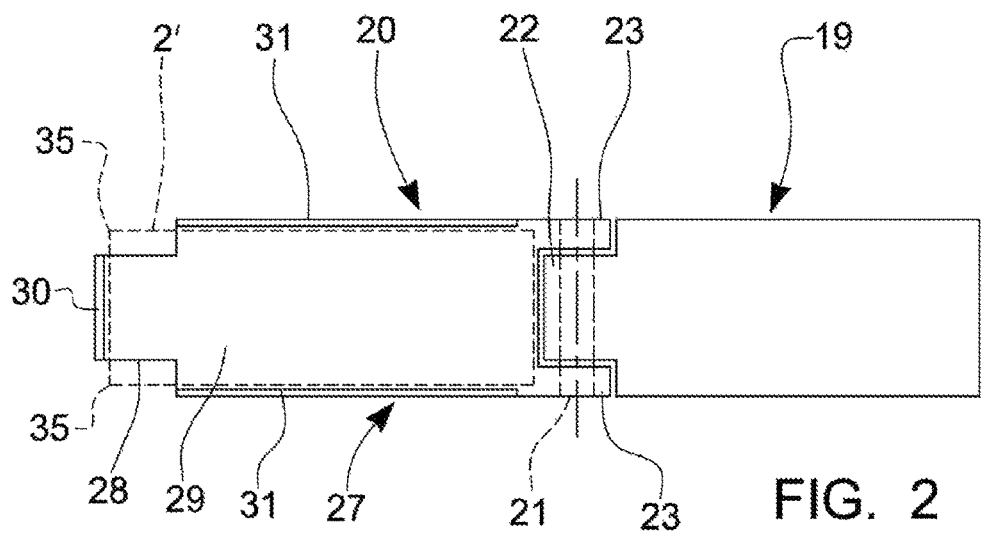
FIG. 2 is a plan view of the displaceable mechanism.

Referring to FIGS. 1 and 2 of the accompanying drawings, a device or slide delivery system 1 for delivering a laboratory sample carrier 2 from a stack 3 of sample carriers according to an embodiment of the invention is illustrated wherein the laboratory sample carrier is a laboratory or microscope slide 2.

The device 1 has a stack retainer 4 for retaining the stack 3 of laboratory slides 2. The stack retainer 4 forms a hopper formed by opposing first and second walls 5, 6 and opposing third and fourth walls (not shown). The hopper 4 is open at its bottom 7 (see FIG. 3).

The device 1 also has an ejector mechanism 8 which includes a base 9 having a top surface 10 and a side surface 11 extending from a bottom of the base 9. A rounded edge 12 is provided between the top surface 10 and the side surface 11, and the side surface 11 is inclined at an angle θ of approximately 15° to the vertical. The angle θ is preferably in the range of 5° to 25° and more preferably in the range of 10° to 20°. A bottom portion of the side surface 11 has a pair of protruding shoulders 13. The top surface 10 has a recess 14 which contains a horizontal linear bearing rail 15, and a carriage 16 is mounted on the rail 15 to form a linear bearing. The carriage 16 is reciprocated back and forth along the rail 15 by a motor 17 via, say, a belt (not shown). The carriage 16 could alternatively be reciprocated by means of a linear actuator. The motor 17 is connected to a processor 18 of the device 1, and the carriage 16 and motor 17 form at least part of a displacement means. A carrier support portion 19 is mounted on the carriage 16 and is hingeably connected to a carrier transporting portion 20 by a pivot connection 21 wherein a tongue 22 of the carrier support portion 19 is held in a yoke 23 of the carrier transporting portion 20 and the pivot connection 21 extends through the tongue 22 and yoke 23. A distal lower corner 25 of the carrier support portion tongue 22 has a rounded edge. The carrier transporting portion 20 is supported by part 26 of the top surface 10 of the base 9 between the recess 14 and the inclined side surface 11 and this part 26 of the top surface 10 forms a carrier transporting portion support. The carrier support portion 19 and the carrier transporting portion 20 together form a displaceable mechanism or hinged platform 27. The carrier transporting portion 20 has a tongue 28 extending from an end distal to the pivot connection 21 and has a carrier accommodating area 29 beneath the hopper 4. The carrier accommodating area 29 is defined by a stop or ridge 30 at the end of the tongue 28 and a pair of shoulders or ridges 31 wherein each shoulder 31 is on an opposite side of the carrier transporting portion 20. The stop 30 is beneath the first wall 5 of the hopper 4. A ball spring 32 in the carrier transporting portion support 26 biases the carrier transporting portion 20 towards the hopper 4. A distal upper corner of the carrier support portion tongue 22 forms an abutment 33 wherein the abutment 33 extends above the carrier accommodating area 29 of the carrier transporting portion 20 at a height of not more than a thickness of the slide 2. The abutment 33 is beneath the second wall 6 of the hopper 4.

The device 1 is positioned above a printer 40 for marking a laboratory slide 2 and the bottom of the inclined side surface 11 of the base 9 of the ejector mechanism 8 of the device 1 is positioned above an entry location 41 of the printer 40 for receiving the slide 2. From the entry location 41, the slide 2 would travel through the printer 2 in a vertical or inclined direction wherein the slide 2 travels under the influence of gravity. The printer 40 is connected to the processor 18 of the device 1 via an electronic interface 42 so that the printer 40 can communicate with the device 1.

In a specific example of a preferred embodiment, the angle θ that the side surface 11 of the base 9 of the device 1 is inclined at is substantially the same as the angle to the vertical of the direction of travel of the slide 2 through the printer 40.

The displaceable mechanism 27 is initially in a first carrier receiving position and configuration, as shown in FIG. 1, wherein the carrier transporting portion 20 of the displaceable mechanism 27 is positioned beneath the hopper 4. A stack 3 of laboratory slides 2, stacked one on top of the other, is placed in the hopper 4 and the lowermost slide 2' is received in the carrier accommodating area 29 of the carrier transporting portion 20.

When a slide 2 is required, the printer 40 sends a request to the processor 18 of the device 1. When the processor 18 receives the request it activates the motor 17 to move the displaceable mechanism 27 from the first carrier receiving position and configuration by the carriage 16 being moved along the rail 15 in a first direction A towards the carrier transporting portion support 26. This causes the abutment 33 of the carrier support portion 19 to push the lowermost slide 2' from the bottom of the stack 3 as the carrier transporting portion 20 is replaced by the carrier support portion 19 beneath the hopper 4 and the first wall or slide stop plate 5 of the hopper 4 prevents the other slides 2 of the stack 3 from being moved. The ball spring 32 reduces friction between the displaceable mechanism 27 and the carrier transporting portion support 26.

Figure 3:
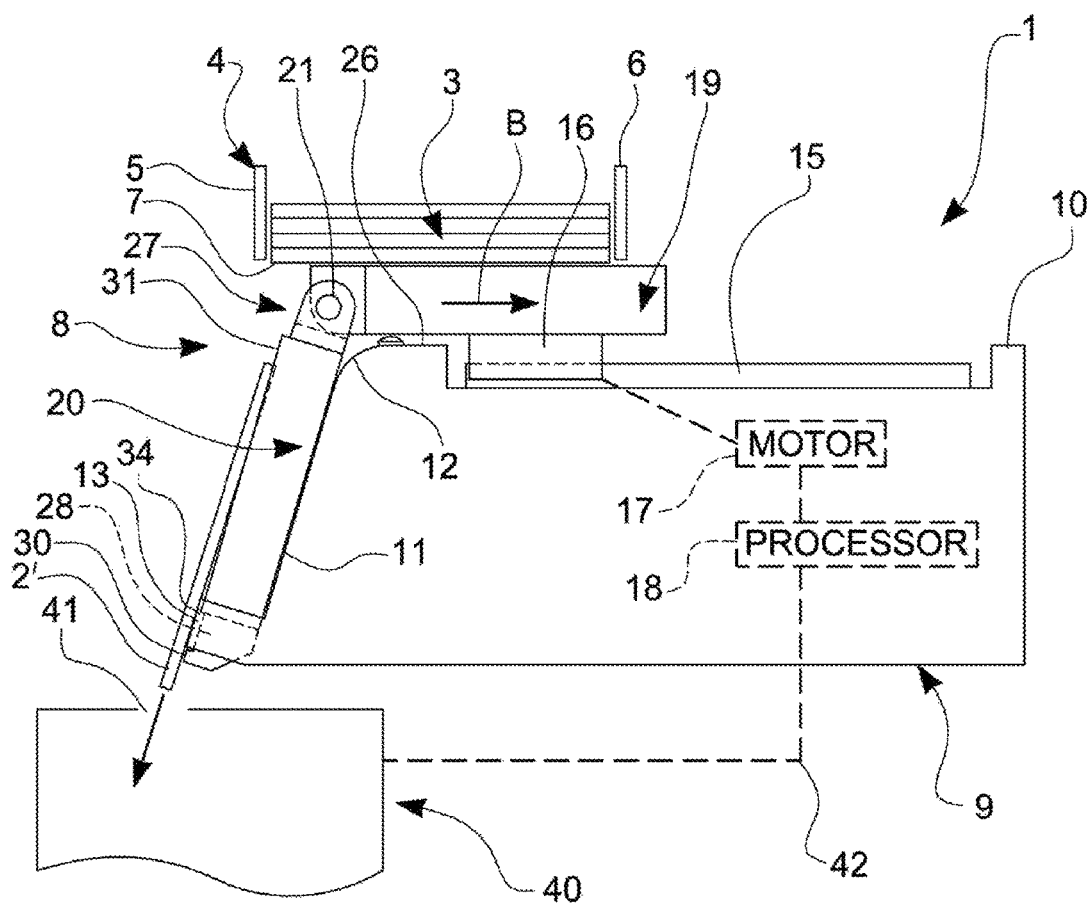
FIG. 3 is a side view of the device and printer, with the displaceable mechanism in a second carrier release position and configuration.

Reference will now be made to FIG. 3 which shows the displaceable mechanism 27 in the second carrier release position and configuration. When the carrier transporting portion 20 is pushed beyond the top surface 10 of the base 9, it is no longer supported by the carrier transporting portion support 26. The carrier transporting portion 20 consequently drops and rotates about the pivot connection 21 relative to the carrier support portion 19 towards the inclined side surface 11 of the base 9. By the distal lower corner 25 of the carrier support portion tongue 22 having a rounded edge, the carrier transporting portion 20 is able to be close to the carrier support portion tongue 22 as it rotates about the pivot connection 21.

As the carrier transporting portion 20 rotates, the stop 30 prevents the slide 2' held in the carrier accommodating region 29 from dropping from the carrier transporting portion 20, and the shoulders 31 restrict sideward movement of the slide 2'. As the carrier transporting portion 20 approaches the inclined side surface 11, the tongue 28 falls between the pair of shoulders 13 extending from the bottom portion of the inclined side surface 11 of the base 9.

As the carrier transporting portion 20 reaches the inclined side surface 11 the surfaces 34 of the shoulders 13 distal from the inclined side surface 11 engage the corners 35 of the slide 2' (shown in dashed lines in FIG. 2) adjacent the stop 30 and displace the slide 2' past the stop 30. The slide 2' is thus released from the carrier transporting portion 20 and falls by gravity into the entry location 41 of the printer 40. The shoulders 31 of the carrier transporting portion 20 guide the slide 2' as it begins to fall towards to the entry location 41. The carrier transporting portion 20 now rests against the inclined side surface 11 of the base 9 and the displaceable mechanism 27 has reached a second carrier release position and configuration.

The motor 17 is then activated to move the displaceable mechanism 27 back to its first carrier receiving position and configuration shown in FIG. 1. As the carriage 16 is moved in a second direction B opposite to the first direction A, the carriage support portion 19 pulls the carrier transporting portion 20 over the rounded edge 12 and under the stack 3 of slides 2 in the hopper 4. When the displaceable mechanism 27 returns to its first carrier receiving position and configuration, the lowermost slide of the stack 3 drops into the carrier accommodating area 29 of the carrier transporting portion 20.

A user is able to manually load a laboratory slide 2 into the entry location 41 of the printer 40 as indicated by dashed arrow 43 in FIG. 1 regardless of whether the displaceable mechanism 27 is in its first carrier receiving position and configuration or is in its second carrier release position and configuration. The user does not need to remove the slides 2 from the stack 3 or remove the hopper 4 or even remove the whole device 1 from the printer 40 to manually load a laboratory slide 2 into the printer 40.

Whilst a particular embodiment has been described, it will be understood that various modifications may be made without departing from the scope of the claimed invention.

The invention claimed is:

1. A device for delivering a laboratory sample carrier from a stack of sample carriers, the device comprising:
    a retainer configured to retain a stack of laboratory sample carriers; and
    an ejector mechanism comprising:
        a carrier support portion and a carrier transporting portion which are hingeably interconnected, the carrier transporting portion having a carrier accommodating region and a stop;
        a motor to displace the carrier support portion from a first carrier receiving position and configuration to a second carrier release position and configuration, the carrier transporting portion arranged to support the stack when the carrier support portion is in the first carrier receiving position and configuration, the carrier support portion arranged to move a lowermost carrier from the bottom of the stack in the carrier accommodating region as the carrier support portion is displaced from the first carrier receiving position and configuration, and the carrier support portion is arranged to support the stack when the carrier support portion is in the second carrier release position and configuration;
        a release surface that releases said carrier from the carrier accommodating region when the carrier support portion reaches the second carrier release position and configuration, wherein the release surface is positioned to engage the carrier in the carrier transporting portion and displace the carrier past the stop of the carrier transporting portion when the carrier support portion reaches the second carrier release position and configuration; and
        a carrier transporting portion support for supporting the carrier transporting portion when the carrier support portion is in the first carrier receiving position and configuration but does not support the carrier transporting portion when the carrier support portion is in the second carrier release position and configuration thereby allowing the carrier transporting portion to drop to a carrier release position to release any said carrier from the carrier accommodating region, wherein the stop of the carrier transporting portion prevents a said carrier held in the carrier accommodating region from dropping from the carrier transporting portion before the carrier support portion reaches the second carrier release position and configuration.

2. A combination of the device of claim 1 and an apparatus for marking a laboratory sample carrier that is arranged to travel through the apparatus vertically or inclined such that the carrier travels under the influence of gravity, and the device being positioned to drop the released carrier into the apparatus for marking.

3. The device as claimed in claim 1, wherein the carrier support portion has an abutment for moving said lowermost carrier from the bottom of the stack.

4. The device as claimed in claim 1, wherein the carrier transporting portion is arranged to rotate relative to the carrier support portion when the motor displaces the carrier transporting portion from the first carrier receiving position and configuration to the second carrier release position and configuration.

5. The device as claimed in claim 1, wherein the carrier transporting portion support is part of a base of the ejector mechanism and the release mechanism comprise part of the base.

6. The device as claimed in claim 1, wherein the carrier transporting portion has a stop for preventing a said carrier held in the carrier accommodating region from dropping from the carrier transporting portion before the carrier support portion reaches the second carrier release position and configuration.

7. The device as claimed in claim 1, wherein the stack retainer comprises a stack retaining stop for preventing carriers other than the lowermost carrier of the stack from being moved when said lowermost carrier is moved from the bottom of the stack.

8. The device as claimed in claim 1, wherein the carrier transporting portion support includes a biasing mechanism that biases the carrier transporting portion towards the retainer that retains the stack of carriers.

9. The device as claimed in claim 1, wherein the apparatus for marking is arranged to receive by hand a carrier to be marked as well as to receive a carrier from the device.

10. A method for delivering a laboratory sample carrier from a stack of sample carriers in the device of claim 1, the method comprising the steps of:
    providing the carrier support portion and the carrier transporting portion which are hingeably interconnected;
    retaining the stack of laboratory sample carriers;
    supporting the stack with the carrier transporting portion and supporting the carrier transporting portion with the carrier transporting portion support when the carrier support portion is in a first carrier receiving position and configuration; and displacing the carrier support portion from the first carrier receiving position and configuration to a second carrier release position and configuration, the displacing step comprising:
    (i) moving a lowermost carrier from the bottom of the stack in a carrier accommodating region of the carrier transporting portion as the carrier support portion is displaced from the first carrier receiving position and configuration;
    (ii) displacing the carrier support portion such that the carrier transporting portion moves past the carrier transporting portion support and drops so that the displaceable mechanism adopts the second carrier release position and configuration and the carrier in the carrier accommodating region is released;
    (iii) supporting the stack with the carrier support portion when the carrier support portion is in the second carrier release position and configuration; and
    (iv) dropping the released carrier into an apparatus for marking a laboratory sample carrier, the released carrier travelling through the apparatus vertically or inclined under the influence of gravity.

* * * * *